United States Patent
Meitav (10) Patent No.: US 10,299,724 B2
(45) Date of Patent: May 28, 2019

(54) WRISTWATCH INCLUDING AN INTEGRATED PULSE OXIMETER OR OTHER MODULES THAT SENSE PHYSIOLOGICAL DATA

(71) Applicant: ams Sensors Singapore Pte. Ltd., Singapore (SG)

(72) Inventor: Ohad Meitav, Sunnyvale, CA (US)

(73) Assignee: ams Sensors Singapore Pte. Ltd., Singapore (SG)

( * ) Notice: Subject to any disclaimer, the term of this patent is extended or adjusted under 35 U.S.C. 154(b) by 643 days.

(21) Appl. No.: 14/787,448

(22) PCT Filed: Apr. 28, 2014

(86) PCT No.: PCT/SG2014/000184
§ 371 (c)(1),
(2) Date: Oct. 27, 2015

(87) PCT Pub. No.: WO2014/178793
PCT Pub. Date: Nov. 6, 2014

(65) Prior Publication Data
US 2016/0073954 A1    Mar. 17, 2016

Related U.S. Application Data

(60) Provisional application No. 61/816,902, filed on Apr. 29, 2013.

(51) Int. Cl.
*A61B 5/1455* (2006.01)
*A61B 5/02* (2006.01)
(Continued)

(52) U.S. Cl.
CPC ............ *A61B 5/681* (2013.01); *A61B 5/0002* (2013.01); *A61B 5/02055* (2013.01);
(Continued)

(58) Field of Classification Search
CPC .............. A61B 5/1455; A61B 5/14551; A61B 5/14552; A61B 5/6801; A61B 5/681; A61B 5/6824; A61B 5/0002
See application file for complete search history.

(56) References Cited

U.S. PATENT DOCUMENTS 5,810,736 A     9/1998   Pail
6,126,595 A *  10/2000   Amano ................. A61B 5/681
                                                        600/322

(Continued)

FOREIGN PATENT DOCUMENTS

EP        0756849        11/2002
WO     2011/013132       2/2011

OTHER PUBLICATIONS

International Search Report and Written Opinion issued by RO/AU in PCT/SG2014/000184 dated Aug. 19, 2014.
(Continued)

*Primary Examiner* — Eric F Winakur
(74) *Attorney, Agent, or Firm* — Fish & Richardson P.C.

(57) ABSTRACT

A wristwatch includes a case containing electronic components of the wristwatch. An optoelectronic module including at least one light emitting element and at least one light sensing element is disposed within the case or within a fastener for the wristwatch. The optoelectronic module is operable to obtain physiological data of a person wearing the wristwatch by using the light emitting element and the light sensing element.

10 Claims, 5 Drawing Sheets

(51) Int. Cl.
*A61B 5/00* (2006.01)
*A61B 5/0205* (2006.01)
*A61B 5/024* (2006.01)

(52) U.S. Cl.
CPC ...... *A61B 5/02427* (2013.01); *A61B 5/14552* (2013.01); *A61B 2560/0406* (2013.01); *A61B 2560/0475* (2013.01); *A61B 2562/0238* (2013.01); *A61B 2562/166* (2013.01)

(56) References Cited

U.S. PATENT DOCUMENTS 8,827,930 B2 * 9/2014 Wekell ................. A61B 5/0002
600/587
2009/0054751 A1 2/2009 Babashan et al.

OTHER PUBLICATIONS

Wrist Watch Finger Pulse Oximeter CMS50F + Data Storage + Software (http://www.amazon.co.uk/Finger-Oximeter-CMS50F-Storage-Software/dp/B004HPDROK), downloaded Apr. 5, 2013.
Pulsoximeter—PULSOX-1 NEW (http://www.anandic.com/docs/index.aspx?id=29008&), downloaded Apr. 5, 2013.
PulseOximetersPlus—What is an Oximeter (http://www.pulseoximetersplus.com/what-is-an-oximeter/), downloaded Apr. 5, 2013.

* cited by examiner

WRISTWATCH INCLUDING AN INTEGRATED PULSE OXIMETER OR OTHER MODULES THAT SENSE PHYSIOLOGICAL DATA

FIELD OF THE DISCLOSURE

This disclosure relates to a wristwatch including a pulse oximeter or other module to sense physiological data.

BACKGROUND

Pulse oximeters are medical devices commonly used in the healthcare industry to measure the oxygen saturation levels in the blood non-invasively. A pulse oximeter can indicate the percent oxygen saturation and the pulse rate of the user.

Pulse oximeters can be used for many different reasons. For example, a pulse oximeter can be used to monitor an individual's pulse rate during physical exercise. An individual with a respiratory condition or a patient recovering from an illness or surgery can wear a pulse oximeter during exercise in accordance with a physician's recommendations for physical activity. Individuals also can use a pulse oximeter to monitor oxygen saturation levels to ensure adequate oxygenation, for example, during flights or during high-altitude exercising.

Modern pulse oximeters, for example, can include a peripheral probe and a microprocessor unit to display a waveform, oxygen saturation and pulse rate. The probe can be placed in contact with an appropriate part of the individual (e.g., a finger). The probe can include multiple light emitting devices such as LEDs, one in the visible red part of the spectrum (e.g., 660 nm) and one in the infrared part of the spectrum (e.g., 940 nm). The beams of light pass through the tissues to one or more photodetectors. The amount of light absorbed by blood and soft tissues depends on the concentration of hemoglobin, and the amount of light absorption at each frequency depends on the degree of oxygenation of the hemoglobin within the tissues.

A variety of types of pulse oximeters are known. However, some of these devices are not particularly convenient to use and can cause discomfort when worn.

SUMMARY

This disclosure describes wristwatches having an integrated pulse oximeter and/or other modules that sense physiological data.

For example, in one aspect, a method of monitoring physiological data of a person includes wearing a wristwatch about a portion of a human body and sensing physiological data of the human body using an optoelectronic module that forms part of the wristwatch. The optoelectronic module includes at least one light emitting element and at least one light sensing element. The method can include emitting a light signal from the optoelectronic module toward the human body and sensing, in the optoelectronic module, a light signal reflected by the human body.

In another aspect, a wristwatch includes a case containing electronic components of the wristwatch. An optoelectronic module including at least one light emitting element and at least one light sensing element is disposed within the case and is operable to obtain physiological data of a person wearing the wristwatch by using the at least one light emitting element and the at least one light sensing element.

In yet another aspect, a wristwatch includes a case containing electronic components of the wristwatch. A strap has a first end connected to the case, and a fastener is connected to another end of the strap. An optoelectronic module is disposed within the fastener and includes at least one light emitting element and at least one light sensing element. The module is operable to obtain physiological data of a person wearing the wristwatch by using the at least one light emitting element and the at least one light sensing element.

Some implementations can provide various advantages. For example, some implementations of the wristwatch can be less cumbersome than other pulse measurement devices. By integrating a pulse oximeter or other sensor modules into a wristwatch, heart-rate or other sensory indicators can be monitored efficiently and relatively easily. Preferably, the user need not wear measurement devices on other parts of his or her body, as the sensors are integrated into the wristwatch.

Other aspects, features and advantages will be readily apparent from the following detailed description, the accompanying drawings and the claims.

DETAILED DESCRIPTION

Figure 1:
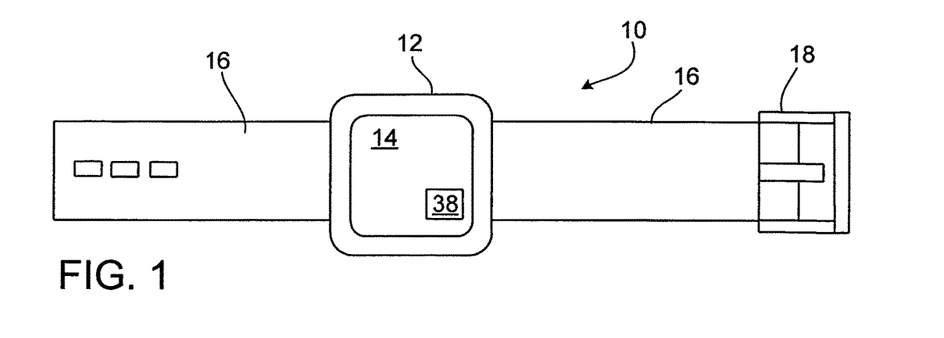
FIG. 1 illustrates an example of a top view of a wrist watch.

As shown in FIG. 1, a wristwatch 10 includes a case 12 that holds various electronics and mechanical components to control operation of the watch. Case 12 may be referred to as a housing in some implementations. A crystal or other transparent cover 14 is provided over the front face of the watch. The front face of the watch provides a digital or analog display for the time, date and other information. A strap 16, which sometimes can take the form of a band or bracelet, is connected to opposite ends of case 12 and is sufficiently long, for example, to be worn around a person's wrist. Attached at one end of strap 16 is a fastener 18, which may be implemented, for example, as a buckle, clasp or clip. The two free ends of strap 16 can be held together in known fashion by use of fastener 18.

Figure 2:
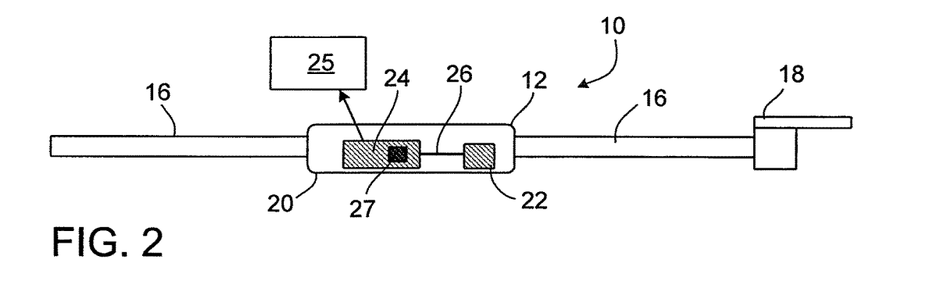
FIG. 2 illustrates a side view of first implementation of a wristwatch that includes a pulse oximeter.

As shown in the side view of wristwatch 10 in FIG. 2, various internal components can be mounted on a main plate 20 that forms part of case 12. In addition to other components of watch 10, a pulse oximeter 22 is mounted within case 12. In some implementations, pulse oximeter 22 is mounted on main plate 20. In such implementations, to allow optical signals to be emitted from and received by pulse oximeter 22, main plate 20 includes a window that is transparent to wavelength(s) of light that pulse oximeter 22 is designed to emit and detect. In other implementations, the transparent window is part of pulse oximeter 22, and main plate 20 includes an opening into which pulse oximeter 22 is inserted. In such implementations, when pulse oximeter 22 is positioned fully within the opening, the outer surface of the transparent window of the pulse oximeter preferably is substantially flush with the outer surface of main plate 20. Further details of a pulse oximeter 22 that can be fabricated with sufficiently small dimensions so that it can fit within case 12 are described below in connection with FIGS. 4 through 7.

A processing unit or data storage unit 24 can be coupled to pulse oximeter 22 so as to receive data from the pulse oximeter and to transmit signals to the pulse oximeter. In the illustrated example, unit 24 is coupled to pulse oximeter 22 by one or more wires 26. Unit 24 can be implemented, for example, as an integrated circuit. Unit 24 also can be configured to store pulse oximeter 22 data, which can be transmitted wirelessly to an external processing and display unit 25. For this purpose, unit 24 can include a wireless transceiver 27 to transmit data to an external data processing or storage unit. In some implementations, unit 24 also has processing capabilities so that data from pulse oximeter 22 can be processed and, in some implementations, displayed on the front face of watch 10. In such situations, unit 24 may include software code to enable processing of the data received from oximeter 22 in accordance with an algorithm stored in memory of unit 24. Such an algorithm can be used, in known fashion, to obtain pulse and oxygen level information from the data received from oximeter 22. Unit 24 can be separate from the processing unit that performs time-keeping functions of watch 10 or can be integrated as part of a single processing unit that performs both time-keeping functions as well as processing of the data from oximeter 22. Pulse oximeter 22 also can be coupled to other components within case 12 of wristwatch 10 for powering of the pulse oximeter.

Figure 3:
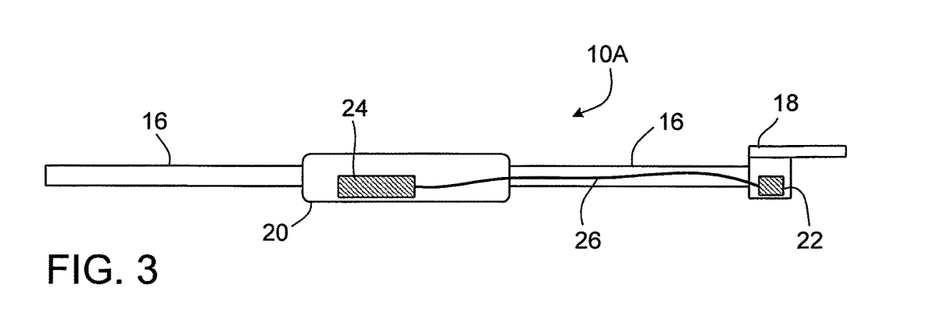
FIG. 3 illustrates a side view of another implementation of a wristwatch that includes a pulse oximeter.

FIG. 3 illustrates another example of a wristwatch 10A that is similar to watch 10, except that pulse oximeter 22 is mounted within fastener 18. Placing pulse oximeter 22 within fastener 18 can be advantageous because, when wristwatch 10 is worn by an individual, it allows the pulse oximeter to be in close contact with the part of the wrist where blood vessels are located, which can make it easier for the pulse oximeter to obtain accurate measurements. In the illustrated implementation, pulse oximeter 22 is coupled to unit 24 by way of one or more wires 26 that are embedded within strap 16. As in the implementation of FIG. 2, unit 24 can be configured to store data, which can be transmitted wirelessly to an external processing unit. In some implementations, unit 24 also has processing capabilities so that data from oximeter 22 can be processed and, in some implementations, even displayed on the front face of watch 10.

In order to allow pulse oximeter 22 to fit within case 12 (FIG. 2) or fastener 18 (FIG. 3), pulse oximeter should have small dimensions. As an example, the lateral dimensions (width and length) of pulse oximeter 22 can be several millimeters (e.g., 2-4 mm), and the height of the pulse oximeter can be even less (e.g., 1.5-2 mm). Examples of a module that can be used as pulse oximeter 22 are described in U.S. Provisional Application No. 61/751,018, which also describes fabrication techniques (e.g., wafer-level techniques) for making such modules. The contents of that application are incorporated herein by reference. FIGS. 4 through 9 illustrate examples of optoelectronic modules that can be used for pulse oximeter 22. Other examples and details are described in U.S. Provisional Patent Application No. 61/751,018, the contents of which are incorporated herein by reference.

Figure 4:
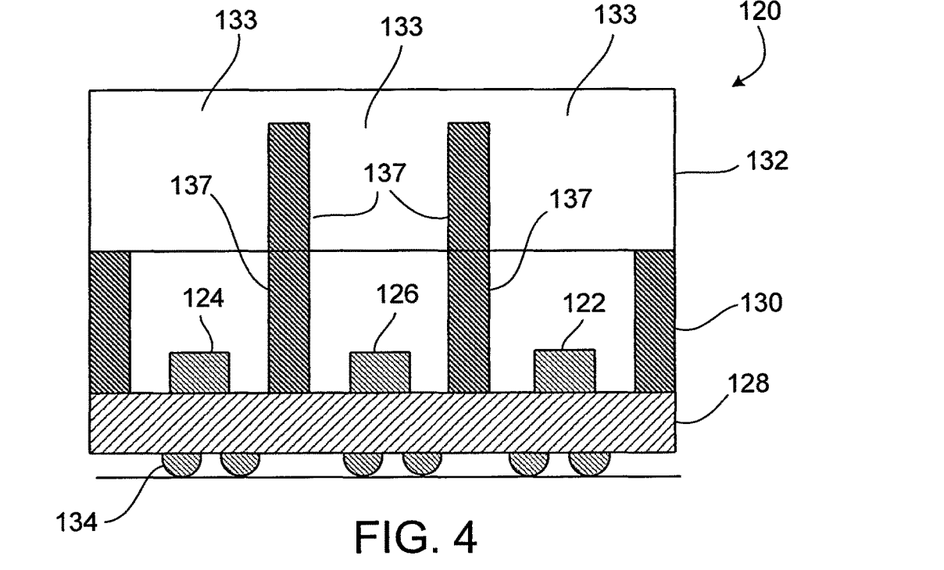
FIG. 4 illustrates a first example of an optoelectronic module for a pulse oximeter.

As illustrated in FIG. 4, a first pulse oximeter module 120 houses multiple active optical components, including a first light emitting element 122, a second light emitting element 124 and a light sensing element 126. Examples of light emitting elements 122, 124 include LEDs, OLEDs and laser chips. Examples of light sensing element 126 include photodiodes and image sensors. Light sensing element 126 can be arranged to sense light at wavelengths or in a range of wavelengths emitted by first and second light emitting elements 122, 124. Light emitting elements 122, 124 may emit light at the same wavelength or at different wavelengths. For example, in some implementations, first light emitting element 122 emits light in the red part of the spectrum (e.g., about 600 nm), whereas second light emitting element 124 emits light in the infra-red (IR) or near-IR part of the spectrum (e.g., in the range of about 700-1100 nm). Different wavelengths or ranges of wavelengths may be used in other implementations.

Module 120 includes several constituents stacked upon each other in the vertical direction. In the example of FIG. 4, module 120 includes a substrate 128, a separation member 130, and a substantially transparent cover glass 132. Substrate 128 can be, for example, a printed circuit board assembly (PCB). On substrate 128 are mounted light emitting elements 122, 124 and light sensing element 126, whose optical axes are separated from another by vertical walls of separation member 130. Thus, separation member 130 laterally encircles each of light emitting elements 122, 124 and light sensing element 126.

Electrical contacts of light emitting elements 122, 124 and light sensing element 126 are connected electrically to outside module 120, where solder balls 134 are attached. Instead of solder balls 134, some implementations include contact pads on substrate 128, which may be provided with solder balls at a later time.

Module 120 can be mounted on a printed circuit board, e.g., using surface mount technology (SMT), next to other electronic components. Module 120 can be manufactured to have a particularly small size and is mass-producible using wafer-level manufacturing techniques.

Separation member 130 may fulfill several tasks in some implementations. It can help ensure a well-defined distance between substrate 128 and cover glass 132 (through its vertical extension) so as to achieve well-defined light paths from light emitting elements 122, 124 through cover glass 132 and from the outside of module 120 through cover glass 132 to light sensing element 126. Separation member 130 also can help provide protection of light sensing element 126 from light external to module 120 that is not supposed to be detected. Separation member 130 also can help provide protection of light sensing element 126 from light emitted by light emitting elements 122, 124 that should not reach the light sensing element, so as to reduce optical cross-talk. In addition, light reflected inside module 120 and stray light originating from light emitting elements 122, 124 can be prevented from reaching light sensing element 126. Such protection can be achieved, for example, by forming separation member 130 of a material that is substantially non-transparent to light generally detectable by light sensing element 126. If module 120 contains more than one light emitting element, the light emitting elements can be placed in separated cavities (as shown in FIG. 4) or can be placed in a common cavity.

Cover 132 is composed primarily of first regions 133 that are transparent to light emitted by light emitting elements 122, 124 and to light that is to be detected by light sensing element 126. Cover 132 also includes second light blocking regions 135 embedded within transparent regions 133. Second regions 135 are located above, and generally aligned with, the internal vertical walls 137 of separation member 130, and are composed of a material that is substantially non-transparent to light emitted by light emitting elements 122, 124 and to light that is to be detected by light sensing element 126. Regions 135 can help reduce optical cross-talk and detection by light sensing element 126 of other undesirable light signals.

Non-transparent second regions 135 extend at least partially through cover 132 in the vertical direction (i.e., in the z-direction) so as to help reduce optical cross-talk. For example, in the illustrated example, non-transparent second regions 135 extend vertically from the bottom surface of cover 132 (i.e., the surface of cover 132 adjacent the top surface of separation member 130) toward its top surface. Although, it may be desirable in some implementations for non-transparent second regions 135 to extend vertically almost to the top of cover 132, a small amount of transparent material can be allowed to remain for structural stability during subsequent handling and processing. Thus, in the illustrated example, regions 135 do not extend all the way to the top surface of cover 132. Non-transparent second regions 135 also can extend substantially through the entire width of cover 132 (i.e., in the y-direction).

In some implementations, non-transparent regions 135 of cover 132 are composed of a polymer material, e.g., a hardenable (e.g., curable) polymer material, such as an epoxy resin. Regions 135 can be composed, for example, of an epoxy containing carbon black to make them substantially non-transparent to light at the desired wavelengths. For example, in some implementations, regions 135 can be made of a UV- or thermally-curing epoxy containing carbon black or other dark pigment. In some implementations, the carbon black is embedded in the epoxy. The amount of carbon black in the epoxy may depend on the particular application and may depend, for example, on the desired or required optical characteristics of regions 135.

The materials described above for light blocking regions 135 of cover 132 also can be used for separation member 130. Thus, in some implementations, light blocking regions 135 and separation member 130 are composed of the same material.

In some implementations, transparent regions 133 of cover 132 are selectively transparent. For example, they can be made of, or coated with, materials that are highly transmissive for the light emitted by the light emitting element(s) 122, 124 and, at the same time, they can be reflective or absorptive for some or all other wavelengths, especially for ambient light like sunlight. This can improve the signal-to-noise ratio.

As illustrated in FIG. 4, module 120 is a packaged opto-electronic component. The vertical side walls of module 120 are formed by substrate 128, separation member 130 and cover 132. A bottom wall is formed by substrate 128, and a top wall by cover 132. Each of substrate 128, separation member 130 and cover 132 can have substantially the same lateral shape and lateral dimensions, which can facilitate an efficient way of manufacturing such modules 120.

Optoelectronic components (i.e., light emitting elements 122, 124 and light sensing element 126) can be either packaged or unpackaged electronic components. For contacting substrate 128, technologies such as wire-bonding or flip chip technology or any other known surface mount technologies may be used, as can conventional through-hole technology.

Figure 5:
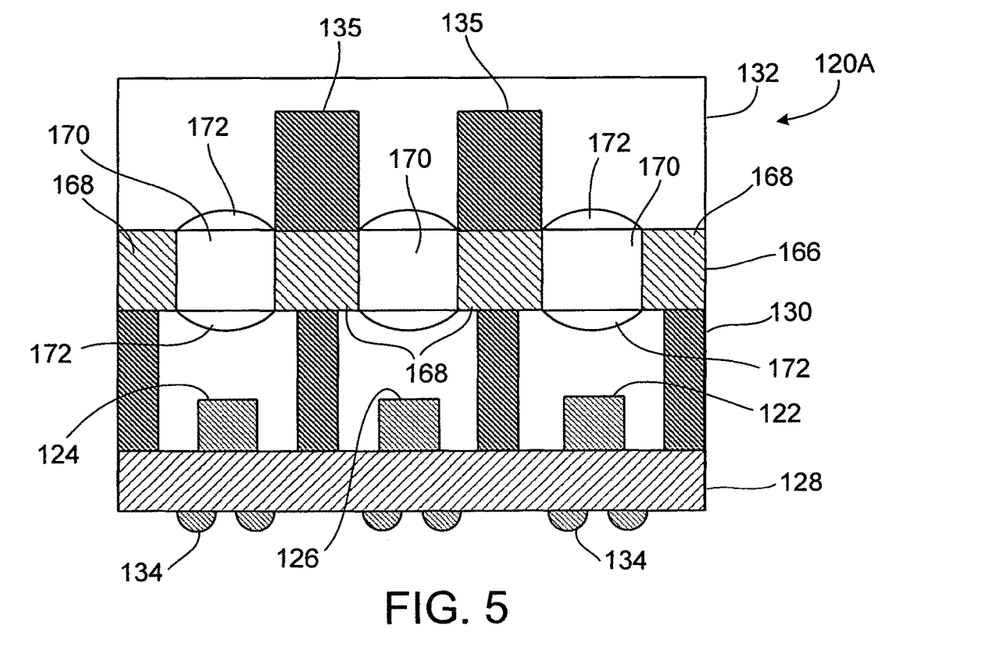
FIG. 5 illustrates a second example of an optoelectronic module for a pulse oximeter.

FIG. 5 illustrates another example of a module 120A that can be used as the pulse oximeter module. Module 120A is similar to module 120 of FIG. 4, but also includes passive optical components. The passive optical components can redirect light by refraction and/or diffraction and/or reflection and can include, for example, a lens, a prism, a mirror or an optical system (e.g., a collection of passive optical components that may include mechanical elements such as aperture stops, image screens or holders). In some implementations, the lenses can further improve crosstalk reduction (e.g., by directing stray light away from the photodiode) and/or can select the sensing depth/area in the object being measured.

As illustrated in FIG. 5, module 120A includes an optics member 166 that has light blocking portions 168, and transparent portions 170 for allowing light emitted by light emitting members 122, 124 to leave module 120A and for allowing light to enter from outside module 120A and reach light sensing member 126. Light blocking portions 168 are substantially non-transparent for light generally detectable by light sensing member 126, e.g., by being made of a suitable (polymer) material. Passive optical elements such as lenses 172 for light guidance or light shaping can be provided on one or both surfaces of each transparent portion 170. In some implementations, a common light shaping element (e.g. lens) is provided for multiple light emitting elements.

Some implementations include neither a separation member 130 nor passive optical elements such as lenses 172. Instead, as shown in the example module 120B of FIG. 6, cover glass 132 can be attached directly to substrate 128, which carries the active optical components (e.g., light emitting elements 122, 124 and light sensing element 126). Cover 132, which is substantially transparent, includes embedded substantially non-transparent regions 135 as described above. Non-transparent regions 135, which are embedded in areas of cover 132 so as to reduce stray light and/or optical cross-talk between components 122, 124 and 126, can be formed as discussed above.

Figure 6:
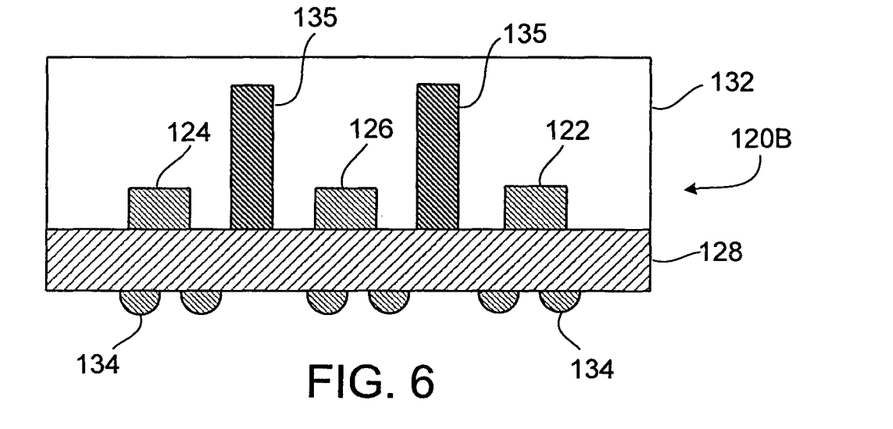
FIG. 6 illustrates a third example of an optoelectronic module for a pulse oximeter.

Modules 120, 120A and 120B are examples of optoelectronic modules that include a substantially transparent cover that allows light to exit and/or enter the module and that includes one or more embedded non-transparent regions to help reduce stray light and/or optical cross-talk between the light emitting and light sensing. The details of other modules that include such a cover may differ. For example, some modules may include a different number of light emitting or light sensing elements (e.g., multiple light sensing elements).

Figure 7:
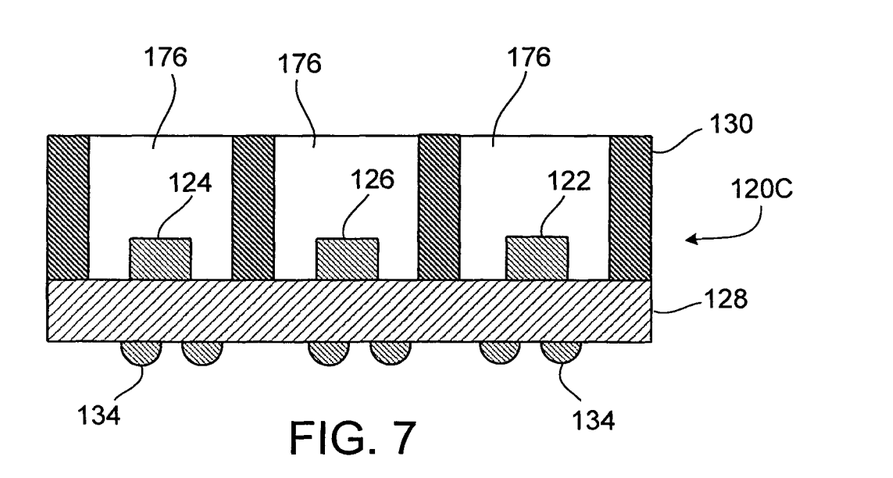
FIG. 7 illustrates a fourth example of an optoelectronic module for a pulse oximeter.

Some implementations of the optoelectronic module for the pulse oximeter may not include cover glass 132 or optics member 166. In that case, as shown in FIG. 7, the upper surface of separation member 130 can serve as the upper surface of the module 120C. As described above, the vertical sidewalls of separation member 130 can help reduce stray light and optical cross-talk between active optical components 122, 124, 126. In addition, to protect active optical components 122, 124, 126, cavities 176 containing the active optical components can be filled (partially or substantially completely) with a solid transparent material (i.e., a material that is substantially transparent to the wavelengths of light emitted by or sensed by active optical components 122, 124, 126).

The modules described above in connection with FIGS. 4 through 7 can be incorporated into wristwatch 10 (e.g., into either case 12 or fastener 18) and used as pulse oximeter 22. Pulse oximeter 22 in combination with processing unit 24 can perform operations based on differential optical absorption spectroscopy (DOAS) by illuminating the skin and measuring changes in light absorption to obtain a photoplethysmogram (PPG). In such applications, spectroscopy is performed in a reflective manner, using one or more off-line wavelengths that exhibit low scattering or absorption and one or more on-line wavelengths that exhibit strong scattering or absorption. The spectroscopy can be performed using the differential signal between the off-line and the on-line wavelengths.

In some implementations, any of the sensor modules (e.g., 120, 120A, 120B, 120C) that serve as pulse oximeter module 22 also can serve as a proximity sensor, which can be used, for example, to detect when wristwatch 10 is in contact with or adjacent a user's skin. In particular, the amount of light detected by light sensing element 126 is indicative of whether or not wristwatch 10 is close to the user's skin (i.e., whether or not a person is wearing the wristwatch). Upon detecting that a user is wearing wristwatch 10 or has removed the wristwatch, module 22 can provide one or more signals to processing unit 24, which can use the received signal(s) to initiate some other function of the wristwatch (e.g., power savings when the wristwatch is removed). Thus, a single sensor module 22 can be used to implement multiple functions.

In some implementations, one or more other sensor modules can be contained within case 12 of wristwatch 10 in addition to module 22. Examples of such other sensor modules include a thermal sensor module and/or a global positioning system (GPS) or accelerometer sensor module.

Figure 8:
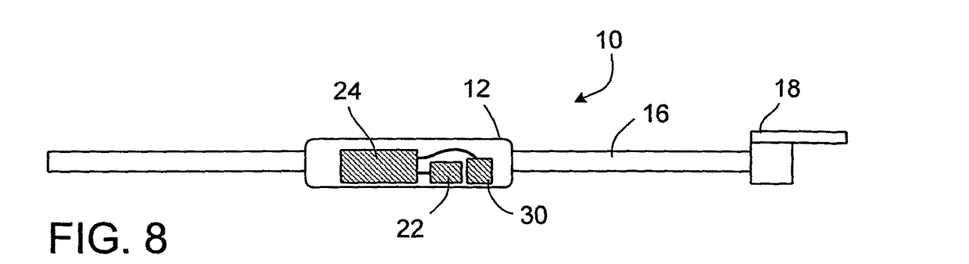
FIG. 8 illustrates a side view of a wristwatch that includes a thermal sensor.

FIG. 8 illustrates an example of a wristwatch 10 that includes a thermal sensor module 30, which can be used, for example, to obtain an ambient temperature or the temperature of the user wearing the wristwatch. If the thermal sensor is arranged to measure ambient temperature, thermal sensor module 30 can include an opening towards the ambient environment. If thermal sensor 30 is arranged to measure body temperature, then module 30 can include an opening towards the body of the person wearing the wristwatch. Data from thermal sensor module 30 can be transferred to processing unit 24, which can combine the temperature data with information from pulse oximeter 22 or other sensor modules. The combined information can be displayed either on the front face of watch 10 or on an external display.

Figure 9:
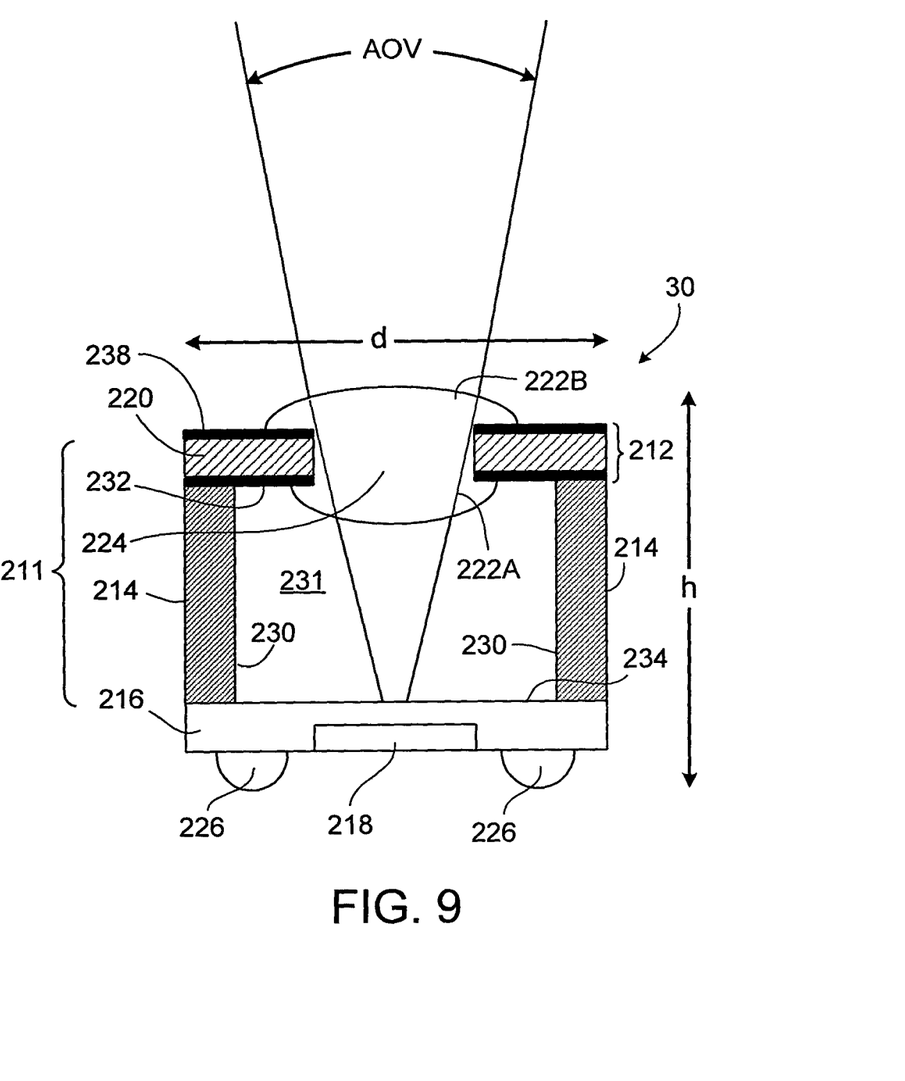
FIG. 9 illustrates an example of a thermal sensor module.

Details of an example of a small thermal sensor module 30 are illustrated in FIG. 9. Although the dimensions of module 30 can vary depending on the particular application, in some cases the overall dimensions (e.g., lateral diameter and height) are on the order of just a few millimeters (mm), for example 5 mm or less. In some implementations, each of the lateral diameter (d) and the height (h) may be as little 2 mm or less. The module's angle of view (AOV) can be, for example, less than 30°.

As illustrated in FIG. 9, thermal sensor module 30 includes an optics part 212 that serves as a cover for the module, a spacer part 214 and a sensor package 216. The combination of optics part 212 and spacer part 214 forms an optical module 211 to which sensor package 216 is attached. Spacer part 214 separates optics part 212 from sensor package 216 and maintains a predetermined axial distance between the optics part and the sensor package.

As shown in the example of FIG. 9, sensor package 216 includes a thermal sensor 218 that detects IR radiation. The underside of sensor package 216 can include external conductive contacts 226 such as solder balls or SMT pads, which can be connected electrically to conductive lines on a printed circuit board (PCB).

Optics part 212 includes an optics substrate 220 (which also can be referred to as a lens substrate), at least a central portion 224 of which is composed of a transparent material (i.e., one that allows IR radiation to pass through). The remainder of optics substrate 220 can be composed, for example, of printed circuit board (PCB) material such as FR4, which is a grade designation assigned to glass-reinforced epoxy laminate material. In some implementations, optics substrate 220 is composed of material that is transparent to IR radiation (e.g., silicon, germanium, GaAs, KBr, $CaF_2$). One or more lens elements are attached to optics substrate 220 such that they are aligned with central transparent portion 224 as well as sensor 218. In the illustrated example, a first lens element 222A is provided at the lower surface 232 of optics substrate 220, and a second lens element 222B is provided at the upper surface 238 of optics substrate 220.

Spacer part 214, which can be attached to optics part 212, has an inner side surface 230 extending between the bottom surface 232 of optics substrate 220 and the top surface of sensor package 234. Inner side surface 230, which can have a cylindrical, parallel-piped or other shape, generally runs perpendicular to lower surface 232 of optics substrate 220 and top surface 234 of sensor package 216. As shown in the example of FIG. 9, lower surface 232 of optics substrate 220, inner side surface 230 of spacer part 214 and top surface 234 of sensor package 216 define an inner area 231 that serves as a channel for incoming radiation. Inner area 231 can protect optical element 222A from environmental influences during manufacture and use, and can shield sensor 218 from ambient infrared radiation. Spacer 214 also forms side walls of the module 30.

In order to reduce detection by sensor. 218 of radiation emitted by the materials that form part of module 30, one or more portions of module 30 are composed of, or coated with, a low emissivity material. Other examples and details of a non-contact thermal sensor module are described in U.S. Provisional Patent Application No. 61/788,478, the contents of which are incorporated herein by reference.

Figure 10:
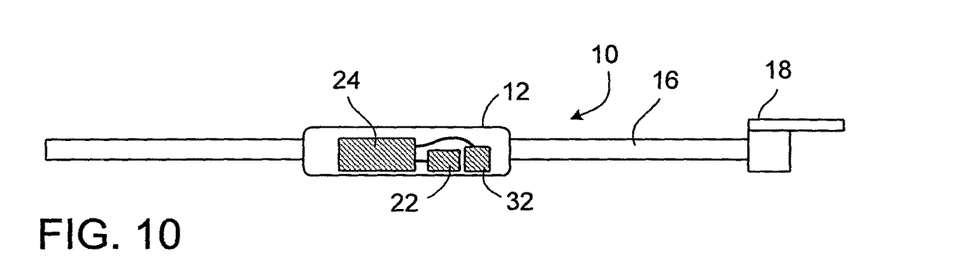
FIG. 10 illustrates an example of a wristwatch that includes a GPS sensor module.

FIG. 10 illustrates an example of a wristwatch 10 that includes a GPS sensor module 32. Pulse oximeter 22 can be used in combination with GPS sensor module 32. For example, GPS sensor module 32 can obtain physical coordinates of a user who is wearing wristwatch 10. The data can be transferred to processing unit 24, which can use the data to determine and monitor the user's distance and speed during a physical workout (e.g., running). This information can be combined with information from pulse oximeter 22. The combined information can be displayed either on the front face of watch 10 or on an external display.

Although FIGS. 8 and 10 show pulse oximeter 22 as being located within case 12, in other implementations pulse oximeter 22 can be located in fastener 18, as shown in FIG. 3.

In some implementations, wristwatch 10 can include an alarm circuit 38 (see FIG. 1) that generates an audible or visual alarm or warning if the processing unit 24 determines that data from the one or more modules 22, 30, 32 is outside of a predetermined range or is within a range indicative of a health risk for the person wearing the wristwatch. For example, processing unit 24 may be programmed to monitor the person's heart rate and oxygen level, as well as other sensory indicators, based on data from modules 22, 30, 32. Processing unit 24 may determine, based on the monitored data, that the person's heart rate and/or oxygen level are outside acceptable ranges and, in response, can trigger alarm circuit 38 to generate an appropriate alarm or warning.

The various wristwatches described above can be less cumbersome than some other pulse measurement devices. By integrating the pulse oximeter or other sensor modules into a wristwatch, heart-rate or other sensory indicators can be monitored efficiently and relatively easily. The user need not wear measurement devices on other parts of his or her body, as the sensors are integrated as part of the wristwatch.

Other implementations are within the scope of the claims.

What is claimed is:

1. A wristwatch comprising:
   a case containing electronic components of the wristwatch;
   a strap connected to the case;
   a fastener connected to the strap; and
   an optoelectronic module including at least one light emitting element and at least one light sensing element, the module operable to obtain physiological data of a person wearing the wristwatch by using the at least one light emitting element and the at least one light sensing element, wherein the optoelectronic module is disposed within the fastener.

2. The wristwatch of claim 1 wherein the case further includes a data storage unit mounted therein, wherein the data storage unit is coupled to the optoelectronic module to store physiological data sensed by the optoelectronic module.

3. The wristwatch of claim 2 wherein the optoelectronic module is coupled to the data storage unit through one or more wires extending through the strap.

4. The wristwatch of claim 2 wherein the data storage unit includes a wireless transmitter to transmit data to an external data processing or storage unit.

5. The wristwatch of claim 1 wherein the case includes a data processing unit mounted therein, wherein the data processing unit is coupled to the optoelectronic module to process physiological data sensed by the optoelectronic module.

6. The wristwatch of claim 5 wherein the data storage unit includes a wireless transmitter to transmit data to an external data processing or storage unit.

7. The wristwatch of claim 1 wherein the optoelectronic module has width, length and height dimensions on the order of four millimeters or less.

8. The wristwatch of claim 1 wherein the optoelectronic module has width, length and height dimensions on the order of two millimeters or less.

9. The wristwatch of claim 1 wherein the optoelectronic module is operable to measure at least one of heart rate or oxygen level of a person wearing the wristwatch.

10. The wristwatch of claim 1 wherein the optoelectronic module is a pulse oximeter.

* * * * *